United States Patent [19]

Smoll

[11] Patent Number: 5,417,119
[45] Date of Patent: May 23, 1995

[54] DUAL ELECTROMAGNET PARTIALLY DISPOSABLE FLUID FLOW TRANSDUCER WITH SIDE-BY-SIDE ELECTRODES

[76] Inventor: Owen C. Smoll, 2470 Stow St., Simi Valley, Calif. 93063

[21] Appl. No.: 178,562

[22] Filed: Jan. 7, 1994

[51] Int. Cl.⁶ .............................................. G01F 1/58
[52] U.S. Cl. ................................ 73/861.12; 73/861.11
[58] Field of Search ........... 73/861.08, 861.11, 861.12, 73/861.15–861.17; 128/691

[56] References Cited

U.S. PATENT DOCUMENTS

| | | | |
|---|---|---|---|
| 3,967,500 | 7/1976 | Forster | 73/861.06 |
| 4,195,515 | 4/1980 | Smoll | 73/861.13 |
| 4,236,411 | 12/1980 | Ketelsen | 73/861.12 |
| 4,346,605 | 8/1982 | Skladzien et al. | 73/861.13 |
| 4,520,650 | 6/1985 | Palmer et al. | 73/3 |
| 4,635,486 | 1/1987 | Jacobsen et al. | 73/861.12 |
| 4,727,754 | 3/1988 | Ruckel | 73/861.12 |
| 4,881,413 | 11/1989 | Georgi et al. | 73/861.12 |
| 5,090,250 | 2/1992 | Wada | 73/861.12 |
| 5,220,841 | 6/1993 | Brown et al. | 73/861.12 |
| 5,325,728 | 7/1994 | Zimmerman et al. | 73/861.12 |

Primary Examiner—Richard E. Chilcot, Jr.
Assistant Examiner—Elizabeth L. Dougherty
Attorney, Agent, or Firm—Robert E. Bushnell

[57] ABSTRACT

An electromagnetic flow meter for measuring the flow of conductive fluids, e.g. blood, in an extracorporeal circuit. The electromagnetic flow meter utilizes two electromagnets positioned in a portion of the housing of a transducer unit, and a disposable insert easily insertable into a cavity of the housing. The electromagnets generate, at any one time, magnetic fields having opposite directions. The conductive fluid flows in a direction perpendicular to the direction of the magnetic fields for inducing first and second voltages. First and second electrodes extend into the bore of the disposable insert and provide the voltages, generated by the fluid flow cutting through the magnetic fields, to first and second pick-up sockets in said housing.

13 Claims, 2 Drawing Sheets

DUAL ELECTROMAGNET PARTIALLY DISPOSABLE FLUID FLOW TRANSDUCER WITH SIDE-BY-SIDE ELECTRODES

BACKGROUND OF THE INVENTION

This invention is related to electromagnetic flow meters, and more specifically, relates to an apparatus used in extracorporeal measurement of blood flow or other conductive liquids.

BACKGROUND OF THE INVENTION

The use of electromagnetic flow meters to measure fluid flow of conductive fluids, such as blood, is well known. A basic concept, for example, is described in U.S. Pat. No. 2,149,847. By passing blood, either in a tube or blood vessel oriented at right angles to a magnetic field, a voltage is produced at right angles to both the magnetic field and in the direction of blood flow. The blood has the property of a moving conductor cutting through a magnetic field. The voltage generated is proportional to the velocity of flow and therefore directly proportional to the volume rate of flow of the fluid. The voltage can be measured by electrodes placed at diametrically opposite points of the tube along a diameter extending perpendicular to the magnetic lines of the flux.

Because the electrodes, magnet structure, and fluid passage must be maintained in a fixed predetermined relationship in order to maintain accurate calibration of the flow measurement, it has been the practice heretofore to assemble the tube, electrodes, and magnet structure as a unit and direct flow of blood or other conductive fluids through the tubular section in making measurements. It has been my observation that such a unitary structure has several disadvantages in extracorporeal use. First, it is difficult to sterilize effectively after use. Also different size units must be provided to accommodate measurements in different size flow lines. Where measurements are to be taken at more than one point in the extracorporeal circuit, a plurality of separate complete flow meter units are required.

My In Line Electromagnetic Flow Measurement Transducer described in U.S. Pat. No. 4,195,515 improved on prior art electromagnetic measuring units by making the unit into separable parts that can be readily assembled and disassembled. One part includes a tube with electrode sensors that can be disposed of, or readily and easily changed and sterilized by conventional techniques. The other part included a magnet structure for generating the required magnetic field, and quick disconnect electrical connections for the electrodes of the tube. The magnetic structure can be used with different size tubular units so that measurements can be made at different points in a extracorporeal circuit wherein different size tubular units are positioned at said different points. The magnetic structure is simply moved from one tubular unit to another.

The magnetic structure in my '515 device is comprised of a C-shaped magnetic core, a coil winding on the core and at least three female connection terminals for connection to at least three male terminals formed from the electrodes of the tubular unit.

The Blood Flow Detection Device described by Donald K. Georgi, et al. in U.S. Pat. No. 4,881,413 is comprised of a reusable transducer unit having at six connectors separately positioned to provide at three connectors on each diametrically opposite side of a tubular unit inserted therein. The transducer unit comprises a single "C" shaped magnet for producing a magnetic field through which the blood flows. The tubular unit has at six electrodes with three electrodes on diametrically opposite sides of the tube and the bore of the tube is narrower in the central section thereof as compared to the end sections. I have noticed that this arrangement of electrodes results in a cumbersome assembly when connecting the tubular unit to the transducer unit. The six electrodes of the disposable tubular units are in contact with the conductive fluid as the fluid flows through the tube. The increased number of electrodes concomitantly increases the surface area of the electrodes in contact with the flowing fluid, thereby causing decreased stability during the measuring process.

SUMMARY OF THE INVENTION

It is therefore, one object of the present invention to provide an improved apparatus for measuring flow of fluid through an extracorporeal circuit.

It is another object to simplify the structure of apparatus electromagnetically measuring flow of fluid through extracorporeal circuits.

It is still another object to provide a device exhibiting an enhanced stability in measurements made of fluid flowing through extracorporeal circuits.

It is yet another object to provide a device that is less cumbersome to assemble, for measuring fluid flow through an extracorporeal circuit.

It is still yet another object to provide a partially disposable device for measuring fluid flow through an extracorporeal circuit.

It is a further object to provide a device easily assembled and disassembled for measuring fluid flow through an extracorporeal circuit, that can be quickly assembled to accommodate different sizes of tubular units.

These and other objects may be attained with an improved electromagnetic measuring unit for making measurements in an extracorporeal circuit. The electromagnetic structure contemplates two electromagnets positioned to establish separate magnetic fields from the same side of a tube and a pair of electrical connections. The tube is disposable and has two side-by-side electrodes extending from the same side of the tube for connection to the pair of electrical connections in the magnetic structure. The windings for each electromagnet are wrapped in opposite directions around each respective core of each electromagnet so that at any given time the magnetic field at one electrode is in an opposite direction to the magnetic field at the other electrode.

The reduced number of electrodes results in an electrode surface area in contact with the conductive fluid ⅔ less than that of the blood flow detection device of U.S. Pat. No. 4,881,413 thereby enhancing flow stability and resulting in less zero base line shift during a measurement process. The electrode arrangement also provides for easier assembly and disassembly between the electromagnetic structure and the tubular unit. Further, the side-by-side electrodes in separate and opposite magnetic fields results in minimized eddy current loops that occur in the device of U.S. Pat. No. 4,881,413 due to the diametrically opposite electrodes being in the same magnetic field and fluid path. The dual electromagnet partially disposable fluid flow transducer with side-by-side electrodes of the present invention has less expensive production costs for both the electromagnetic structure and the disposable tubular unit than that of the Bioprobe.

BRIEF DESCRIPTION FOR THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
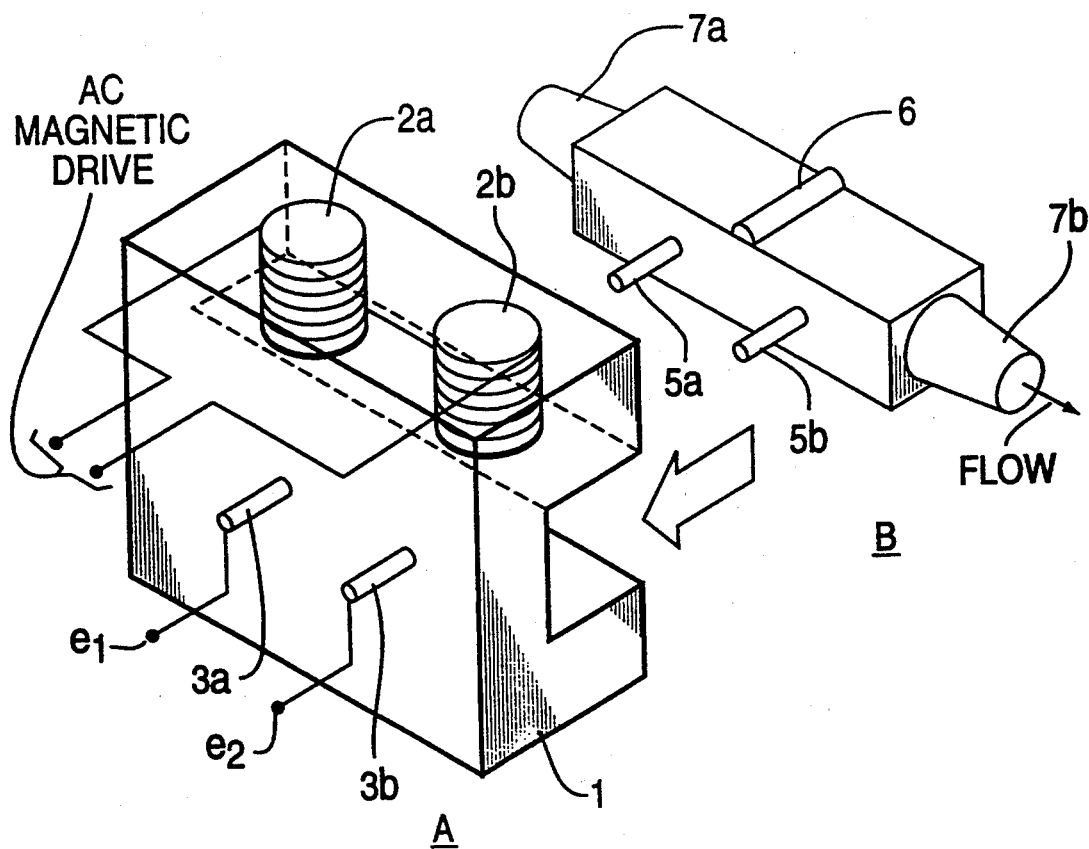
FIG. 1 is a perspective view of a flow meter wherein the electromagnetic structure and the tubular unit are shown in a disassembled condition.

Referring to FIG. 1, the flow meter assembly comprises a transducer unit A and a disposable/replaceable insert B. The transducer unit A is comprised of an electromagnetic housing 1 having a blocked "C" shape, a pair of electromagnets 2a and 2b are disposed in an upper portion of the electromagnetic housing 1 and position over the "C" opening, and a pair of pick-up sockets 3a and 3b disposed in a central portion of said electromagnetic housing 1.

The insert B is comprised of a rectangular central section 4 having a tubular bore of constant diameter, a pair of side-by-side electrodes 5a and 5b extend through the central section 4 into the bore and extend diametrically, or radially, away from the central section 4 to form male connectors for insertion into the pick-up sockets 3a and 3b, respectively. The insert B is further comprised of conical tubular members 7a and 7b each having bore diameter equal to that of central section 4, wherein the conical tubular members 7a and 7b are respectively formed on each end of the central section 4. The central member 4 has at least one key 6 on a side orthogonal to the side having the electrodes 5a and 5b for enabling the insert B to be inserted into the transducer unit A in only one way. The insert B is positioned in an extracorporeal circuit so that a conductive fluid, e.g. blood, flows into member 7a and is discharged from member 7b. Insert B will have a constant bore diameter but that diameter may vary in accordance with its intended use.

Figure 2:
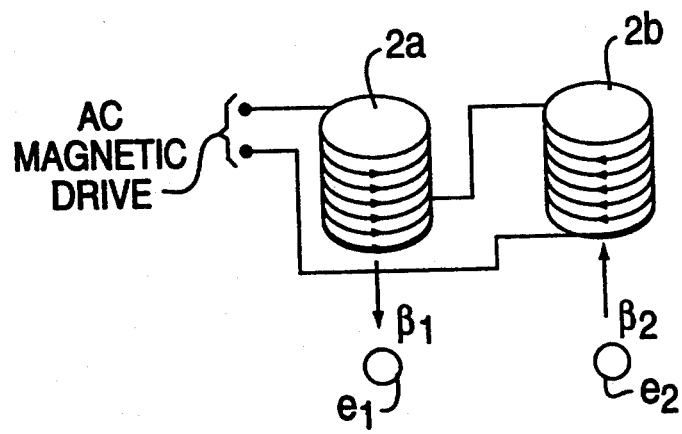
FIG. 2 illustrates the relationship of the cores of each of the electromagnets and their respective windings.

FIG. 2 illustrates the relationship of the windings for electromagnets 2a and 2b. The winding is wrapped around the core of electromagnet 2a in a first direction, e.g. counterclockwise, and is wrapped around the core of electromagnet 2b in a second direction opposite the first direction, e.g. clockwise. Electromagnet 2a will produce a magnetic field $\beta_1$ and electromagnet 2b will produce a magnetic field $\beta_2$ opposite to magnetic field $\beta_1$.

In operation, the insert B fits snugly into the "C" opening of the transducer unit A and the electrodes 5a and 5b marry up with pick-up sockets 3a and 3b, respectively. Key 6 fits into a slot (not shown) in the transducer unit A designed to receive the key 6. An AC, alternating-current, electromagnet drive signal is applied to the windings of the electromagnets 2a and 2b now positioned over the insert B. Conductive fluid flowing through the insert B passes at right angles to magnetic fields $\beta_1$ and $\beta_2$, and 9 voltage is produced at right angles to the direction of conductive fluid flow. The conductive fluid has the property of a moving conductor cutting through a magnetic field. Each electrode 5a and 5b, placed diametrically on the same side of the insert B extending perpendicular to the magnetic lines of the flux, respectively output a separate voltage $e_1$ and $e_2$ via pick-up sockets 3a and 3b, respectively, for measurement. The generated voltages $e_1$ and $e_2$ are proportional to the velocity of flow and therefore directly proportional to the volume rate of flow of the conductive fluid.

Figure 3:
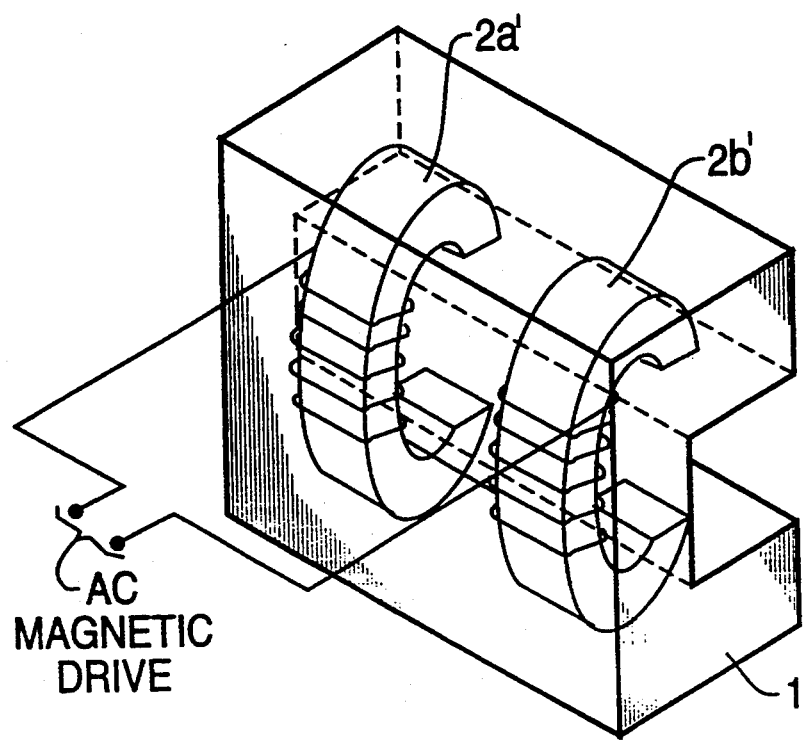
FIG. 3 illustrates an alternative embodiment of the electromagnets housed in the electromagnetic structure of FIG. 1.

A further embodiment, FIG. 3, is comprised of the transducer unit 1 housing a pair of "C" shaped electromagnets 2a' and 2b' each having parallel ends forming the poles on diametrically opposite sides of the insert, the cores of the electromagnets being wrapped in opposite directions by a single winding, wherein the insert contains two electrodes.

Having specifically described a preferred embodiment of the invention, it will be apparent that the invention is not limited to such embodiment, and that modifications and variations may be effected therein by one skilled in the art without departing from the spirit or scope of the present invention as defined in the appended claims.

What is claimed is:

1. An electromagnetic flow meter for measuring blood flow, comprising:

transducer means having a blocked "C" shaped housing, said transducer means comprising a first electromagnet with a winding wrapped around said first electromagnet in a first direction, a second electromagnet with said winding wrapped around said second electromagnet in a second direction, said winding for receiving a driving signal, a first pick-up socket and a second pick-up socket; and insert means for insertion into an extracorporeal circuit comprising a rectangular central section having a constant tubular bore, said central section being insertable into a cavity of said transducer means, a first electrode and a second electrode extending into said tubular bore of said central section for contacting said blood, said first electrode and said second electrode being spaced apart from each other on one side of said central section along the same diametrical plane, said first and second electrodes extending radially outward from said one side of said central section for forming first and second connectors for insertion into said first and second pick-up sockets, respectively;

said insert means having first and second end portions each having a conical shape for enabling said insert means to be inserted into said extracorporeal circuit, said first and second end portions each having a constant tubular bore diametrically equal to the constant tubular bore of said central section for enabling said blood to flow unimpaired through said insert means.

2. The electromagnetic flow meter as set forth in claim 1, said insert means further comprising a key formed on a side orthogonal to the one side from which said first and second electrodes extend.

3. The electromagnetic flow meter as set forth in claim 1, said first and second electromagnets being positioned over said cavity of said transducer means for generating magnetic fields having opposite directions of flow perpendicular to the flow of said blood flowing through said insert means, in response to said driving signal.

4. The electromagnetic flow meter as set forth in claim 3, said first electrode for providing a first voltage to said first pick-up socket in response to said blood flowing perpendicular to said magnetic field produced by said first electromagnet.

5. The electromagnetic flow meter as set forth in claim 3, said second electrode for providing a second voltage to said second pick-up socket in response to said blood flowing perpendicular to said magnetic field produced by said second electromagnet.

6. The electromagnetic flow meter as set forth in claim 3, said first electrode for providing a first voltage to said first pick-up socket in response to said blood flowing perpendicular to said magnetic field produced by said first electromagnet, and said second electrode for providing a second voltage to said second pick-up socket in response to said blood flowing perpendicular to said magnetic field produced by said second electromagnet.

7. A disposable insert for an electromagnetic flow meter having a transducer unit formed by a blocked "C" shaped housing, said transducer unit comprising a first electromagnet with a winding wrapped around a core of said first electromagnet in a first direction, a second electromagnet with said winding wrapped around a core of said second electromagnet in a second direction, said winding receiving a driving signal, and said housing having a first pick-up socket and a second pick-up socket, electromagnetic flow meter measuring fluid flow of a conductive fluid, said disposable insert comprising:

a rectangular central section having a tubular bore of constant diameter, said central section being insertable into a cavity of said blocked "C" shaped housing;

a first electrode and a second electrode extending into said tubular bore of said central section for contacting said conductive fluid, said first electrode and said second electrode being spaced apart from each other on one side of said central section along the same diametrical plane, said first and second electrodes extending radially outward from said one side of said central section for forming first and second connectors for insertion into said first and second pick-up sockets, respectively; and first and second end portions each having a conical shape for enabling said insert to be inserted into an extracorporeal circuit, said first and second end portions each having a constant tubular bore diametrically equal to the constant diameter of said tubular bore of said central section for enabling said conductive fluid to flow unimpaired through said insert means.

8. The disposable insert as claimed in claim 7, further comprising a key formed on a side orthogonal to the one side from which said first and second electrodes extend for ensuring said disposable insert is inserted into said cavity in a predetermined manner.

9. The disposable insert as claimed in claim 7, further comprising said first electrode providing a first voltage to said first pick-up socket in response to said conductive fluid flowing perpendicular to a first magnetic field produced by said first electromagnet, and said second electrode providing a second voltage to said second pick-up socket in response to said conductive fluid flowing perpendicular to a second magnetic field produced by said second magnet, a direction of flow for said first magnetic field being opposite to a direction of flow for said second magnetic field.

10. An electromagnetic flow meter comprising a transducer and a disposable insert for measuring blood flow in an extracorporeal circuit, said transducer comprising:

a blocked "C" shaped magnet housing having a cavity in which said disposable insert is to be inserted;

a first electromagnet with a winding wrapped around a first core in a first direction;

a second electromagnet with said winding wrapped around a second core in a second direction opposite said first direction;

said winding receiving a driving signal for enabling said first electromagnet to generate a first magnetic field and for enabling said second electromagnet to generate a second electromagnetic field, a direction of flow for said first magnetic field being opposite to a direction of flow for said second magnetic field;

said first and second electromagnets being positioned in an upper portion of said blocked "C" shaped housing over said cavity;

a first pick-up socket; and a second pick-up socket;

said first and second sockets extending from a central portion of said blocked "C" shaped magnet housing.

11. The electromagnetic flow meter as set forth in claim 10, said disposable insert comprising:

a rectangular central section having a tubular bore of constant diameter, said central section being insertable into said cavity of said blocked "C" shaped housing;

a first electrode and a second electrode extending into said tubular bore of said central section for contacting said blood, said first electrode and said second electrode being spaced apart from each other on a same side of said central section along the same diametrical plane, said first and second electrodes extending radially outward from said one side of said central section for forming first and second connectors for insertion into said first and second pick-up sockets, respectively; and first and second end portions each having a conical shape for enabling said disposable insert to be inserted into said extracorporeal circuit, said first and second end portions each having a constant tubular bore diametrically equal to the constant diameter of said tubular bore of said central section for enabling said blood to flow unimpaired through said insert means.

12. The electromagnetic flow meter as set forth in claim 11, said disposable insert further comprising one key formed on at least one side of said central section, said at least one side being orthogonal to the side from which said first and second electrodes extend for ensuring said disposable insert is inserted into said cavity in a predetermined manner.

13. The electromagnetic flow meter as set forth in claim 11, said disposable insert further comprising said first electrode providing a first voltage to said first pick-up socket in response to said blood flowing perpendicular to said first magnetic field produced by said first electromagnet, and said second electrode providing a second voltage to said second pick-up socket in response to said blood flowing perpendicular to said second magnetic field produced by said second magnet.

* * * * *